United States Patent [19]

Knorr

[11] 4,323,705

[45] Apr. 6, 1982

[54] PROCESS FOR THE PREPARATION OF N,N'-DIFORMYLHYDRAZINE

[75] Inventor: Harald Knorr, Gersthofen, Fed. Rep. of Germany

[73] Assignee: Hoechst Aktiengesellschaft, Frankfurt, Fed. Rep. of Germany

[21] Appl. No.: 199,456

[22] Filed: Oct. 22, 1980

[30] Foreign Application Priority Data

Oct. 26, 1979 [DE] Fed. Rep. of Germany ....... 2943264

[51] Int. Cl.³ .............................................. C07C 97/16
[52] U.S. Cl. ................................................... 564/151
[58] Field of Search ......................................... 564/151

[56] References Cited

U.S. PATENT DOCUMENTS 3,023,241   2/1962   Twelves .............................. 564/151

OTHER PUBLICATIONS

Ainsworth et al. J. Am. Chem. Soc. 77 (1955) p. 621–623.

Primary Examiner—Arthur P. Demers
Attorney, Agent, or Firm—Connolly and Hutz

[57] ABSTRACT

The invention provides an improved process for the preparation of N,N'-diformylhydrazine of the formula

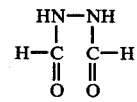

from the hydrazine hydrate and formamide, which comprises operating in two temperature steps and under reduced pressure in order to remove rapidly the ammonia formed from the system. A very pure product is obtained in a yield of above 95%, relative to hydrazine hydrate.

2 Claims, No Drawings

PROCESS FOR THE PREPARATION OF N,N'-DIFORMYLHYDRAZINE

N,N'-diformylhydrazine of the formula

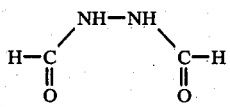

is an intermediate for the manufacture of 1,2,4- triazole which for its part is an important starting material for herbicidal and fungicidal products.

Generally, N,N'-diformylhydrazine is obtained by reacting hydrazine hydrate with formamide at elevated temperature (C. Ainsworth and R. G. Jones, J. Amer. Chem. Soc. 77, 621-4 (1955). After a reaction time of about 2 hours, a reaction mixture is formed about 80% of which consist of the intended product. In order to obtain this product in pure form, alcohol must be added, thus causing by-products, for example N-aminotriazole, to be dissolved. This purification step requiring absolutely the addition of a solvent must be considered as special disadvantage of the process, because the solvent must be regenerated especially in the case of operations on an industrial scale. Moreover, formation of by-products in amounts of 20% (their amount increases still further with increasing size of batches) unfit for further use and thus lost cannot be tolerated in an industrial process.

It was therefore an object of the invention to find an improved method for the synthesis of N,N'-diformylhydrazine in order to allow manufacture on an industrial scale. Another object was to attain a substantially complete conversion, which is an important condition for further processing to triazole, and avoids expensive purification and separation of substance mixtures.

These objects have been achieved in accordance with the present invention.

It has been found that N,N'-diformylhydrazine can be prepared with very high yields when ensuring the ammonia set free in the reaction of hydrazine hydrate with formamide to be rapidly removed from the system.

The invention provides therefore an improved process for the preparation of N,N'-diformylhydrazine of the formula

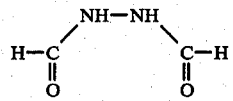

by reaction of formamide with hydrazine hydrate, which comprises mixing first formamide and hydrazine hydrate in a molar ratio of from 2:1 to 2:0.6 at a temperature of from 5° to 25° C., and abandoning this mixture at the same temperature under reduced pressure until splitting- off of ammonia seems to be terminated, raising then the temperature to 80°-120° C. and allowing the reaction to continue for 1 to 3 hours also under reduced pressure, and finally distilling off water and unreacted starting material under a pressure reduced still further.

It was not to be expected that establishing a vacuum would be advantageous for the manufacturing method; for, it had to be feared that under these reaction conditions the hydrazine hydrate, being easily volatile, would distil off before reacting with the formamide.

Formamide and hydrazine hydrate are used in a molar ratio of from 2:1.2 to 2:0.6, preferably 2:0.8 to 2:1.0. The hydrazine hydrate may alternatively be used in the form of aqueous solutions having generally a strength of about 80%.

The reaction is carried out in two steps. In the first step, formamide and hydrazine hydrate are reacted with each other at temperatures of from 5° to 25° C. and under reduced pressure. When splitting-off of ammonia seems to have terminated, which is generally the case after 1 to 2 hours, the temperature is raised to 80°-120° C., preferably 100° C., while maintaining the vacuum, and in the second step the reaction is completed at the cited temperature within a further 1 to 3, preferably 1 to 2, hours. According to a preferred operation mode, the reaction is carried out in the first step at 70-600 mbar and at 5-70 mbar in the second step. The reaction being complete, water and unreacted starting material are distilled off while reducing the pressure still further. Thus, a practically pure N,N'-diformylhydrazine is obtained with a yield of above 95%, relative to hydrazine hydrate.

The following examples illustrate the invention.

EXAMPLE 1

10 mols of formamide (450 g) and 250 ml of hydrazine hydrate (about 80% strength in water) are introduced together into the reactor at room temperature. With thorough agitation, a vacuum is immediately established, which adjusts itself to about 150 mbar. The batch is abandoned at room temperature for 1 hour, thus causing the pressure to reduce itself to 70 mbar, then it is heated to 100° C., at which temperature it is maintained for 1 hour ½in vacuo, after which time a pressure of 13 mbar has adjusted itself. Under this reduced pressure, water and unreacted starting material are distilled off. After drying of the residue in vacuo at 115° C., 351 g of N,N'-diformylhydrazine (97.3%, relative to 100% hydrazine hydrate) are obtained having a melting point of 159° C. (lit.: 159°-160° C. or 160° C.).

COMPARATIVE EXAMPLE

The components are combined as in Example 1 and maintained for 2 hours at 100° C. without reducing the pressure. The volatile components are then distilled off, and 1,000 ml of ethanol are added. On cooling, 273 g of N,N'-diformylhydrazine having a melting point of 158° C. crystallize. In the filtrate, 7.7% of N-aminotriazole, 12.3% of N,N'-diformylhydrazine and 36.1% of formamide are detected among others. The total amount of N,N'-diformylhydrazine is therefore 294 g (81.5%, relative to hydrazine).

EXAMPLE 2

1.375 ml of about 80% hydrazine hydrate and 2.250 g of formamide are introduced at 20° C. into a laboratory mixer having a capacity of 5 liters (Loedige mixer). Subsequently, a vacuum is established, so that a pressure of about 150 mbar adjusts itself. The gaseous ammonia which develops is removed and condensed. The reaction is allowed to proceed for a further hour, within which time the pressure reduces itself to about 100 mbar, and then the batch is heated in an oil bath to 100° C. A pressure of about 79 mbar establishes itself which then reduces to 20 mbar. The batch is maintained for 2 hours at this temperature while water distills off. Subsequently, the oil bath temperature is raised to 140° C., and further water and excess formamide are distilled off within 5 hours until a final pressure of 4 mbar is attained. The total amount of distillate is about 287 g.

1.964 g of N,N'-diformylhydrazine having a melting point of 157° C. are obtained in the form of a colorless, pulverulent mass.

What is claimed is:

1. In a process for the preparation of N,N'-diformylhydrazine of the formula

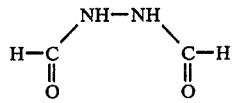

by reaction of formamide and hydrazine hydrate with splitting off of ammonia, the improvement which comprises mixing first formamide and hydrazine hydrate in a molar ratio of from 2:1 to 2:0.6 at a temperature of from 5° to 25° C., and maintaining this mixture at the same temperature under reduced pressure until splitting-off of ammonia is completed, then raising the temperature to 80°–120° C. and allowing the reaction to continue for 1 to 3 hours also under reduced pressure, and finally distilling off water and unreacted starting material under a pressure reduced still further.

2. The process as claimed in claim 1, which comprises operating at 5° to 25° C. at a pressure of from 70 to 600 mbar, and then at 80° to 120° C. at a pressure of from 5 to 70 mbar.